United States Patent
Lin

(10) Patent No.: US 6,727,494 B2
(45) Date of Patent: Apr. 27, 2004

(54) METHOD AND APPARATUS FOR DETECTING CONTAMINATING SPECIES ON A WAFER EDGE

(75) Inventor: Ying-Chuan Lin, Pin-tong (TW)

(73) Assignee: Taiwan Semiconductor Manufacturing Co., Ltd., Hsin Chu (TW)

(*) Notice: Subject to any disclaimer, the term of this patent is extended or adjusted under 35 U.S.C. 154(b) by 283 days.

(21) Appl. No.: 09/837,124

(22) Filed: Apr. 18, 2001

(65) Prior Publication Data

US 2002/0153482 A1 Oct. 24, 2002

(51) Int. Cl.[7] .................... H01J 49/00; B08B 3/00; G01N 35/00
(52) U.S. Cl. .................... 250/282; 250/281; 438/745; 436/43; 436/47; 436/52; 134/2; 134/10; 134/22.14; 134/32; 134/48; 134/71; 134/79; 134/80
(58) Field of Search .................... 250/281, 282; 438/745; 436/43.47, 52; 134/2.1, 22.14, 32.48, 71.79, 80

(56) References Cited

U.S. PATENT DOCUMENTS

| 4,556,317 A | * | 12/1985 | Sandland et al. | ........ 356/237.1 |
|---|---|---|---|---|
| 4,586,743 A | * | 5/1986 | Edwards et al. | ........... 294/86.4 |
| 4,647,764 A | * | 3/1987 | Chadwick et al. | .......... 250/216 |
| 6,239,038 B1 | * | 5/2001 | Wen | ........................... 438/745 |
| 6,375,758 B1 | * | 4/2002 | Nakashima et al. | .......... 134/30 |
| 2001/0007259 A1 | * | 7/2001 | Nakashima et al. | .......... 134/32 |
| 2002/0131166 A1 | * | 9/2002 | Woo et al. | .................. 359/391 |
| 2002/0153482 A1 | * | 10/2002 | Lin | ............................. 250/281 |
| 2002/0182883 A1 | * | 12/2002 | Gilton et al. | ................ 438/745 |
| 2003/0013199 A1 | * | 1/2003 | Anderson et al. | ............. 436/50 |
| 2003/0024883 A1 | * | 2/2003 | Mullee | ....................... 210/661 |
| 2003/0049500 A1 | * | 3/2003 | Takai et al. | .................. 428/702 |

* cited by examiner

Primary Examiner—John R. Lee
Assistant Examiner—Bernard Souw
(74) Attorney, Agent, or Firm—Tung & Associates

(57) ABSTRACT

A method and an apparatus for detecting contaminating species such as metal particles on a wafer edge from a semiconductor fabrication process are disclosed. In the method, a wafer is suspended and rotated in a container with a volume of solvent at a bottom portion of the container such that only an edge portion of the wafer is exposed to the solvent. After the wafer is turned in the solvent such that the entire edge portion of the wafer has been exposed to the solvent, the solvent may be removed for analyzing in an electronic instrument for detecting the species of contaminating particles. The apparatus further includes a wafer mounting device for supporting the wafer which can be adjusted in height to suit wafers of different diameters.

18 Claims, 1 Drawing Sheet

METHOD AND APPARATUS FOR DETECTING CONTAMINATING SPECIES ON A WAFER EDGE

FIELD OF THE INVENTION

The present invention generally relates to a method and an apparatus for detecting contaminating species on a semiconductor wafer and more particularly relates to a method and apparatus for detecting metal particles on a wafer edge by exposing the wafer edge to an acid solution and then analyzing the acid solution.

BACKGROUND OF THE INVENTION

In the fabrication of semiconductor devices, one of the most important aspects of increasing yield of a fabrication process is to reduce defect density, defined as the number of defects per square centimeter of wafer surface area. The defects on the surface of a wafer found during wafer processing are attribute by various forms of contamination. For instance, particle contamination including those of metal particles or non-metallic ions amounts to more than 80% of all defects. The detection of such contamination on a wafer surface becomes even more important as device technology goes down to the sub-micron range, i.e. 0.25 $\mu$m or below. The ability to detect wafer contamination is therefore of utmost importance to the fabrication of semiconductor devices.

In recent development in fabrication technology, the scaling down of devices to dimensions suitable for sub-half micron technology has a serious effect on manufacturing yield and reliability of the integrated circuits produced. The processing complexity increases with each generation of chips, partially caused by the need for additional mask layers to form interconnects for the increased number of sub-circuits designed on the chip. This makes the IC devices more susceptible to contamination introduced by particulate, ions and chemical impurities occurred at each processing step. Moreover, smaller devices produced are more vulnerable to smaller defects and smaller amounts of chemical impurities that may result in unacceptable chip quality. The cleanliness of a wafer surface during processing, or the amount of contaminants on the wafer surface, must be closely monitored to ensure the quality of the IC devices fabricated.

In order to monitor the amount of contaminants of trace organic or inorganic impurities on a wafer surface, such as $Cl^-$, $F^-$ and $SO_4^{--}$, etc, a wafer surface must be pretreated by rinsing or immersing in ultra-pure water or other suitable solvent to dislodge the contaminants. A sample of the ultra-pure water containing the impurities is then analyzed by ion chromatography, gas chromatography or mass spectrometer analysis. Conventionally, a sample is obtained on a wafer by dripping a solvent on the wafer surface directly while the wafer is exposed to ambient air which may itself contain contaminants. Results achieved by the conventional method of analysis is poor and the accuracy of contaminant determination is grossly inadequate due to additional deposition of particulate contaminants on the wafer surface during sample collection. Moreover, when devices such as micro-pipette is used to transport sample solution from a wafer surface to a sample collection bottle, incomplete or inadequate transfer further results in quantitative determination error. There has not been any reliable method proposed in the industry for collecting contaminant samples from a wafer edge.

Metal particle contaminations of a semiconductor wafer surface can seriously deteriorate electrical characteristics of the semiconductor devices formed. For instance, a deterioration may be caused in the breakdown voltage of a gate oxide or in the P—N junction leakage current. Metal particles such as Fe, Cu, Co, Na and other metal particles which are contaminating sources may be produced by the chemicals used in the previous fabrication process or may be produced by the fabricating equipment. Presently, the only method available for detecting the contaminating of wafer by metal particles is limited to a detection on the top surface of the wafer. There is no reliable method for detecting any contamination occurring at the wafer edge which frequently happens after a copper sputtering process and a backside cleaning process. For instance, Co is frequently used in forming contacts on a wafer, while Cu is frequently used in forming via interconnect on the wafer surface. A cross-contamination of the two different metal particles during subsequent processes can cause serious defects in semiconductor devices fabricated. The capability for detecting contamination on a wafer edge therefore becomes an important requirement for insuring the reliability of a fabrication process that involves metal deposition.

It is therefore an object of the present invention to provide a method for detecting contaminating species on a wafer edge that does not have the drawbacks or shortcomings of the conventional methods.

It is another object of the present invention to provide a method for detecting metal particles on a wafer edge that cannot be detected by the conventional detection methods.

It is a further object of the present invention to provide a method for detecting contaminating metal particles on a wafer edge by providing a solvent container for exposing the wafer edge to a solvent.

It is another further object of the present invention to provide a method for detecting contaminating metal particles on a wafer edge by exposing the wafer edge to a diluted HF solution for removing metal particles and then analyzing the solution.

It is still another object of the present invention to provide a method for detecting contaminating metal particles on a wafer edge by first mounting the wafer to a support structure and then exposing the wafer edge to a diluted acid solution for removing metal particles from the wafer edge.

It is yet another object of the present invention to provide an apparatus for collecting contaminating species from a wafer edge that is less than 10 mm from the outer periphery of the wafer.

It is still another further object of the present invention to provide an apparatus for collecting contaminating metal particles from a wafer edge that includes a container for holding a volume of a solvent and a wafer mounting device for supporting a wafer over the container with only a predetermined edge portion of the wafer exposed to the solvent.

It is yet another further object of the present invention to provide an apparatus for collecting contaminating metal particles from a wafer edge by utilizing a solvent container that has an arcuate bottom formed with a radius between about 10 cm and about 15 cm for holding either a 200 mm diameter wafer or a 300 mm diameter wafer.

SUMMARY OF THE INVENTION

In accordance with the present invention, a method and an apparatus for detecting contaminating species on a wafer edge are provided.

In a preferred embodiment, a method for detecting contaminating species on a wafer edge can be carried out by the steps of providing a wafer that has contaminating species on an edge portion, providing a container that has a cavity therein for holding a volume of a solvent, exposing the edge portion of the wafer to the volume of solvent, and analyzing the volume of solvent and determining the contaminating species.

The method for detecting contaminating species on a wafer edge may further include the steps of providing a rotatable shaft that has a first end that is free and a second end that is attached to a bearing mounted in a support structure, the support structure has an adjustable height, mounting the wafer at a center point to the first free end of the rotatable shaft, positioning the wafer vertically in the container and adjusting a height of the bearing such that only a predetermined edge portion of the wafer is exposed to the volume of solvent and rotating the wafer with the edge portion contacting the volume of solvent by turning the rotatable shaft. The method may further include a step of filling the container with a volume of solvent that includes an acid, or filling the container with a volume of solvent that includes HF, or filling the container with a volume of solvent that includes HF in water at less than 20 volume percent concentration.

The method for detecting species on a wafer edge may further include step of exposing an edge portion that is less than 10 mm wide on the wafer to the volume of volume, or the step of exposing the edge portion that is between about 1 mm and about 3 mm wide on the wafer to the volume of solvent. The method may further include a step of analyzing the volume of solvent by an inductively coupled plasm mass spectrometer. The method may further include a step of providing the container with an arcuate bottom formed with a radius between about 10 cm and about 15 cm. The method may further include a step of mounting the wafer at a center point of the wafer by vacuum means, or by a vacuum suction cup. The method may further include the step of rotating the wafer by turning the rotatable shaft by a motor means.

The present invention is further directed to an apparatus for collecting contaminating species from a wafer edge which includes a container that has a cavity therein for holding a volume of a solvent, and a wafer mounting device for supporting a wafer over the container such that only a predetermined edge portion is exposed to the volume of solvent.

In the apparatus for collecting contaminating species from a wafer edge, the container may be provided with an arcuate bottom formed with a radius between about 10 cm and about 15 cm. The volume of solvent may include an acid, or include HF in water at less than 20 volume percent concentration. The predetermined edge portion may be less than about 10 mm wide, or may be between about 1 mm and about 3 mm wide. The apparatus may further include a rotatable shaft that has a free end and a fixed end, the fixed end being rotatable in a bearing that is mounted in a support structure, and means for rotating the wafer by rotating the rotating shaft. The free end of the rotatable shaft may be further equipped with a vacuum means for attaching to the wafer.

BRIEF DESCRIPTION OF THE DRAWINGS

These and other objects, features and advantages of the present invention will become apparent from the following detailed description and the appended drawings in which.

DETAILED DESCRIPTION OF THE PREFERRED EMBODIMENT

Figure 1:
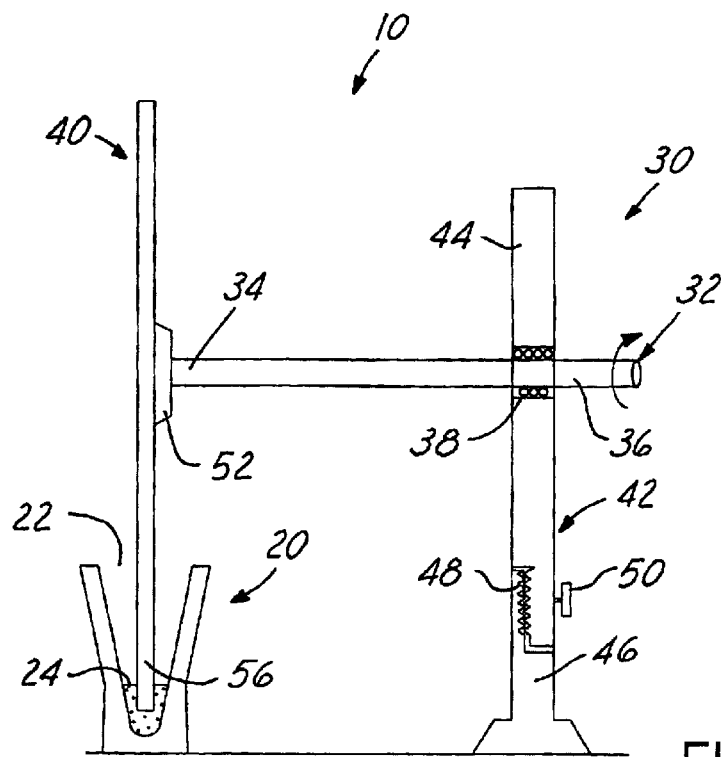
FIG. 1 is a graph illustrating a present invention apparatus for collecting contaminating species from a wafer edge that includes a container and a wafer mounting device.

The present invention discloses a method for detecting contaminating species on a wafer edge which can be carried out by first providing a wafer that has contaminating species on an edge portion, providing a container that has a cavity therein for holding a volume of solvent, exposing the edge portion of the wafer to the volume of solvent and analyzing the volume of solvent to determine the contaminating species.

The method may further include the step of providing a rotatable shaft that has a first free end and a second fixed end rotatably engaging a bearing mounted in a support structure. The support structure has an adjustable height which may be suitably adjusted for wafers of different size. A wafer is then mounted at a center to the first free end of the rotatable shaft by a vacuum means, such as a vacuum suction cup. The wafer is then vertically positioned in the solvent container and the height of the rotatable shaft is adjusted such that only a predetermined width of the edge portion of the wafer is exposed to the volume of solvent. The wafer is then rotated with the edge portion contacting the volume of solvent by turning the rotatable shaft.

The invention further discloses an apparatus for collecting contaminating metal particles from a wafer edge which consists of two major components of a solvent container and a wafer mounting device. The solvent container has a cavity for holding a volume of a solvent, such a diluted acid, while the wafer mounting device is used for supporting a wafer suspended over the container such that only a predetermined width of the edge portion is exposed to the volume of solvent.

The present invention novel apparatus provides a small tank that is filled with a diluted acid solution, such as HF for removing metal particles or any other acid for removing other types of particles. The solvent first removes the metal particles from the wafer edge, the contaminants or the particles are then filtered out and are analyzed in an instrument such as a vapor phase decomposition-inductive coupled plasma-mass spectrometer (VPD-ICP/MS) for detecting the contamination level of metal particles, i.e. such as Cu or Co. The method is particularly suited for determining any possible cross-contamination between Co and Cu in a semiconductor fabrication process wherein Co is used for forming contacts while Cu is used for forming via interconnects. However, the present invention novel apparatus and method can be used to detect any other metal particles on the edge portion of a wafer, which cannot be detected by a conventional detection method such as by vapor phase decomposition alone.

In the present invention novel apparatus, a concave container that has an arcuate bottom with a radius between about 10 cm and about 15 cm is provided for collecting samples from wafers of 200 mm diameter size and 300 mm diameter size. A wafer mounting structure is utilized which has an adjustable support member for setting a wafer vertically inside the solvent container such that only a predetermined width of the edge portion is submerged in the solvent. For a 200 mm diameter wafer, the width of the edge potion submerged in the solvent may be between about 5 mm and about 10 mm. For a 300 mm diameter wafer, the edge portion that is submerged in the solvent may be 3 mm wide.

Figure 2:
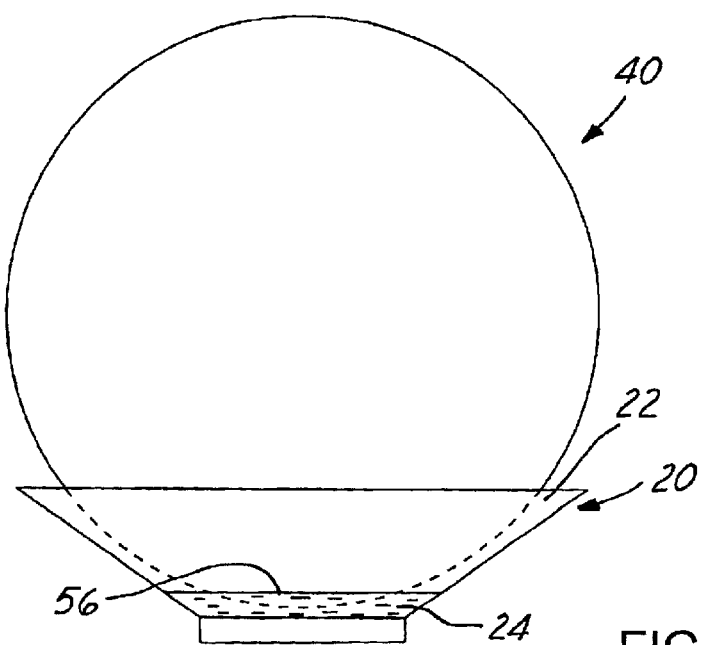
FIG. 2 is an end view of the present invention apparatus of FIG. 1 showing the wafer situated in the solvent container.

Referring initially to FIG. 1, wherein a present invention novel apparatus 10 for colleting contaminating metal particles from a wafer is shown in a side view. The apparatus 10 is constructed by two major components, i.e. a solvent container 20 and a wafer mounting device 30. The solvent container 20 has a cavity 22 therein for holding a volume of solvent 24. An end view of the container 20 and the wafer 40 is shown in FIG. 2.

The wafer mounting device 30 is used for supporting a wafer 40 over the container such that only a predetermined edge portion, such as an edge portion of less than 10 mm wide, is exposed to the volume of solvent 24. The wafer mounting device 30 is further constructed by a rotatable shaft 32 that has a free end 34 and a fixed end 36. The fixed end 36 rotatably engages a bearing 38 that is mounted in a support structure 42. The support structure 42 consists of two major portions, i.e. an upper portion 44 and a lower portion 46 which are engaged together by gear means 48 and fixed by a fixing means 50 such that the height of the support structure 42 can be suitably adjusted based on the different diameter wafers it carries. The free end 34 of the rotatable shaft 32 is further provided with a vacuum means 52, such as a vacuum suction cup. The vacuum means 52 is used for attaching to a center of the wafer 40 such that the wafer 40 can be supported, i.e. suspended in the solvent container 20, as shown in FIG. 1.

The rotatable shaft 32 may be suitably rotated by hand such that the wafer 40 is turned in the volume of solvent 24, or can be rotated by a motor means at a low speed, i.e. a speed less than 10 rpm. The optional motor means is not shown in FIG. 1.

The cavity 22 of the container 20 is filled with a volume of solvent 24, which may be a solvent that contains an acid such as HF in a dilution of less than 20 volume percent concentration, and preferably at less than 5 volume percent concentration. Other suitable acids, or any other suitable solvents may also be used depending on the types of the contaminating particles to be dislodged from the wafer. As shown in FIG. 1, the edge portion 56 of the wafer 40 is immersed in the volume of solvent 24 such that any metal particle on the edge portion 56 can be removed. This is also shown in FIG. 2.

After the edge of wafer 40 is submerged in the volume of solvent 24 for a suitable time period, i.e. such as 1–5 minutes, the volume of solvent 24 may be removed and analyzed either directly or filtered to detect the metal particles. A suitable analyzing technique is by vapor phase decomposition-inductive coupled plasma mass spectrometer (VPD-ICP/MS) technique. In a preferred embodiment, a dummy wafer or a bare wafer is utilized for testing the contamination of a process chamber, i.e. a sputter chamber or a backside cleaning chamber.

The present invention novel apparatus and method for detecting contaminating species such as metal particles on a wafer edge processed in a semiconductor fabrication process have therefore been amply described in the above description and in the appended drawings of FIGS. 1 and 2.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

The embodiment of the invention in which an exclusive property or privilege is claimed are defined as follows.

What is claimed is:

1. A method for detecting contaminating species on a wafer edge comprising the steps of:

providing a wafer having contaminating species on an edge portion;

providing a container having a cavity therein for holding a volume of a solvent;

providing a rotatable shaft having a first end that is free and a second end that is attached to a bearing mounted in a support structure, said support structure having an adjustable height;

mounting said wafer at a center point to said first end of the rotatable shaft;

positioning said wafer vertically in said container and adjusting a height of said bearing such that only a predetermined edge portion of the wafer is exposed to said volume of solvent;

rotating said wafer with said edge portion contacting said volume of solvent by turning said rotatable shaft; and analyzing said volume of solvent and determining said contaminating species.

2. A method for detecting contaminating species on a wafer edge according to claim 1 further comprising the step of filling said container with a volume of solvent that comprises an acid.

3. A method for detecting contaminating species on a wafer edge according to claim 1 further comprising the step of filling said container with a volume of solvent that comprises HF.

4. A method for detecting contaminating species on a wafer edge according to claim 1 further comprising the step of filling said container with a volume of solvent that comprises HF in water at less than 20 vol. %.

5. A method for detecting contaminating species on a wafer edge according to claim 1 further comprising the step of exposing an edge portion that is less than 10 mm wide on the wafer to said volume of solvent.

6. A method for detecting contaminating species on a wafer edge according to claim 1 further comprising the step of exposing an edge portion that is between about 1 mm and about 3 mm wide on the wafer to said volume of solvent.

7. A method for detecting contaminating species on a wafer edge according to claim 1 further comprising the step of analyzing said volume of solvent by an inductively coupled plasma mass spectrometer.

8. A method for detecting contaminating species on a wafer edge according to claim 1 further comprising the step of providing said container with an arcuate bottom formed to a radius between about 10 cm and about 15 cm.

9. A method for detecting contaminating species on a wafer edge according to claim 1 further comprising the step of mounting said wafer at a center point by vacuum means.

10. A method for detecting contaminating species on a wafer edge according to claim 1 further comprising the step of mounting said wafer at a center point by a vacuum suction cup.

11. A method for detecting contaminating species on a wafer edge according to claim 1 further comprising the step of rotating said wafer by turning said rotatable shaft by a motor means.

12. An apparatus for collecting contaminating species from a wafer edge comprising:

a container having a cavity therein for holding a volume of a solvent; and a wafer mounting device for supporting a wafer over said container such that only a predetermined edge portion is exposed to said volume of solvent, said wafer mounting device further comprises a rotatable shaft having a free end and a fixed end, said fixed end being rotatable in a bearing that is mounted in a support structure; and means for rotating said wafer by rotating said rotatable shaft.

13. An apparatus for collecting contaminating species from a wafer edge according to claim 12, wherein said container being provided with an arcuate bottom formed with a radius between about 10 cm and about 15 cm.

14. An apparatus for collecting contaminating species from a wafer edge according to claim 12, wherein said volume of solvent comprises an acid.

15. An apparatus for collecting contaminating species from a wafer edge according to claim 12, wherein said volume of solvent comprises HF in wafer at less than 20 vol. %.

16. An apparatus for collecting contaminating species from a water edge according to claim 12, wherein said predetermined edge portion is less than 10 mm wide.

17. An apparatus for collecting contaminating species from a wafer edge according to claim 12, wherein said predetermined edge portion is between about 1 mm and about 3 mm wide.

18. An apparatus for collecting contaminating species from a wafer edge according to claim 12, wherein said free end of the rotatable shaft is further equipped with a vacuum means for attaching to said wafer.

* * * * *